United States Patent [19]

Wullbrandt et al.

[11] Patent Number: 5,767,255

[45] Date of Patent: Jun. 16, 1998

[54] GLUCOSE- AND SOPHOROSE-LIPIDS, A PROCESS FOR THEIR PREPARATION AND THEIR USE

[75] Inventors: Dieter Wullbrandt, Hofheim; Carlo Giani, Frankfurt; Andreas Brakemeier, Braunschweig; Siegmund Lang, Braunschweig; Fritz Wagner, Braunschweig, all of Germany

[73] Assignee: Hoechst Aktiengesellschaft, Frankfurt am Main, Germany

[21] Appl. No.: 650,852

[22] Filed: May 20, 1996

[30] Foreign Application Priority Data

May 29, 1995 [DE] Germany ............... 195 18 982.5

[51] Int. Cl.$^6$ ............... C07H 1/00; C07H 15/04; C07H 13/04; C07G 3/00

[52] U.S. Cl. .............. 536/18.5; 536/18.6; 536/119; 536/120; 536/123.1; 536/123.13; 536/124; 435/255.4

[58] Field of Search .............. 536/18.5, 18.6, 536/120, 119, 123.1, 123.13, 124; 435/255.4

[56] References Cited

U.S. PATENT DOCUMENTS 4,215,213   7/1980   Inoue et al. ............... 536/115

FOREIGN PATENT DOCUMENTS 6-100581   4/1994   Japan.

OTHER PUBLICATIONS

*Yukagaku* (1991), 40 (9), 709–14.
*Phytochemistry*, vol. 27, No. 7, pp. 2199–2204, 1988.
Carbohydrate Research (1972), 25(1), 59–65.
Methods in Carbohydrate Chemistry (19930, 9, 87–9.
Biotechnology Letters, vol. 13, No. 4, pp. 235–240 (1991).
Gorin et al, "Hydroxy Fatty Acid Glycosides of Sophorose from Torulopsis Magnoliae", Can. J. Cehm. vol. 39, 1961, pp. 846–855.
Hommel, "Formation and physiological role of biosurfactants produced by hydrocarbon–utilizing microorganisms", Biodegrdation 1, pp. 107–119, 1990.
Heinz et al, *Organikum*, VEB Deutscher Verlag der Wissenschaften, Berlin, 1986, pp. 256–257, 432–433, 494.
Matsumara et al. "Surface Activities, Foam Suppression, Biodegradability and Antimicrobial Properties of '-Alkyl glucopyranosides", Yukagaku, 40:9 91991) pp. 709–714.
Leontein et al. "Determination of the Absolute Configuration of Sugars by Gas–Liquid Chromatography of Their Acetylated 2–Octyl Glycosides", Methods Carbohydr. Chem., 9:40 (1993) pp. 87–89.

Sigurskjold et al. "Hydrolysis of Substrate Analogues Catalysed by beta–D–Glucosidase from *Aspergillus niger*. part III Alkyl and Aryl beta–D–Glucopyranosides" Acta Chem. Scand 46 (1992) pp. 451–458.
Brakemeier et al. "Novel Sophorose Lipids From Microbial Conversion of 2–Alkanols", Biotechnol. Lett., 17:11 (1995) pp. 1183–1188.

*Primary Examiner*—John Kight
*Assistant Examiner*—Everett White
*Attorney, Agent, or Firm*—Foley & Lardner

[57] ABSTRACT

The present invention relates to glucose- and sophorose-lipids of the formula I

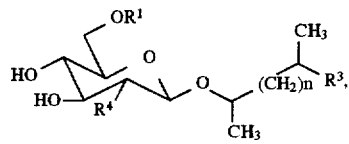

in which $R^4$ is —OH or a group of the formula II,

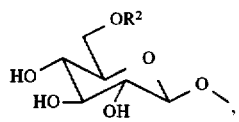

n is an integer from 2 to 26, $R^1$ and $R^2$ are, independently of one another, H or

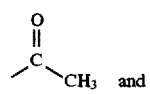

$R^3$ is H or —OH in the case where $R^4$ is —OH, and is H or —OH or a group of the formula III,

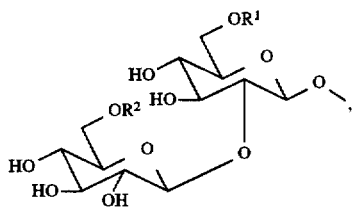

in the case where $R^4$ is a group of the formula II, to a process for obtaining them by fermentation, and to their use as surfactants.

22 Claims, No Drawings

GLUCOSE- AND SOPHOROSE-LIPIDS, A PROCESS FOR THEIR PREPARATION AND THEIR USE

BACKGROUND OF THE INVENTION

1. Field of the Invention

The present invention relates to a novel glucose- and sophorose-lipid, to a process for their preparation by fermentation and to their use as surfactants.

2. Description of Related Art

Microbial glycolipids have been known for some years as biosurfactants with versatile applications in cosmetics, detergents and cleaners, foodstuffs and in the field of environmental protection. They are produced by bacteria, yeasts or fungi when grown on long-chain petroleum products, on vegetable oils and fats or their derivatives, or on mono- and oligosaccharides. Targeted modification of the molecular structures of these products by altering the carbon source to date has been possible to only a slight extent. Since its discovery in 1961, sophorose-lipid has been among the intensively researched microbial glycolipids (P. A. Gorin, J. F. T. Spencer and A. P. Tulloch; Cand. J. Chem, 39 (1961), 846–855).

According to various reports, sophorose-lipid can be produced by various yeasts of the genus Candida (Torulopsis) as secondary metabolite using a substrate from the carbon sources indicated above. Suitable yeast strains described are Candida bombicola, Candida bogoriensis, Candida magnoliae, Candida gropengiesseri and Candida apicola 4(R. Hommel, Biodegradation, 1, (1991), 107).

The sophorose-lipids produced by the genus Candida have a structure (1) depicted below.

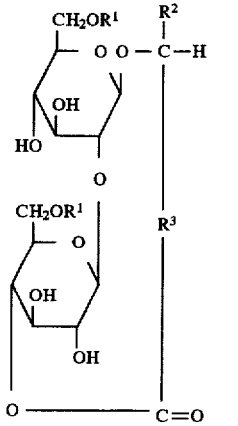

$R^1$=—C(O)CH$_3$, H $R^2$=—CH$_3$, H $R^3$=—(CH$_2$)$_n$—, n=13–16,

—(CH$_2$)$_6$—CH=CH—(CH$_2$)$_7$— or

—(CH$_2$)$_3$—CH=CH—CH$_2$—CH=CH—(CH$_2$)$_7$— (1)

Besides this main lactone product with a hydroxy fatty acid which is linked both glycosidically and in the manner of an ester, also found in small amounts are uncyclized intermediates. Depending on the substrate employed, the hydroxy fatty acid can be saturated, mono- or else polyunsaturated. Furthermore, the 6'—O and 6"—O positions of the glucose units are acetylated to varying extents. Only slight differences in the fatty acids in the side chain of these sophorose-lipids are found.

To produce a glycolipid with amphiphilic structure, i.e., high surface activity, the sophorose-lipid lactones must be converted into the sophorose-lipid esters or amides by elaborate synthetic and purification stages (S. Inoue, et al. U.S. Pat. No. 4,215,213, 1990; Y. Ishigami, JP Application: Toku Kai Hei 6-100581).

SUMMARY OF THE INVENTION

One object of the present invention is to overcome the disadvantages of the known art. Another object of the present invention is to produce glucose- and sophorose-lipids with surface active properties. Still another object of the present invention is to provide a method for producing the glucose- and sophorose-lipids according to the present invention. Still another object is to produce a surfactant which contains the lipids according to the present invention.

In accomplishing the foregoing objects, there has been provided according to the present invention, a compound of the formula I

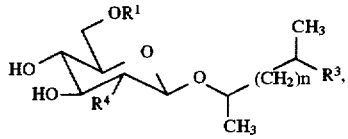

in which $R^4$ is —OH or a group of the formula II,

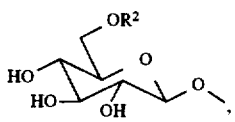

n is an integer from 2 to 26, $R^1$ and $R^2$ are, independently of one another, H or

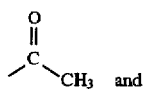

$R^3$ is H or —OH in the case where $R^4$ is —OH, and is H or —OH or a group of the formula III

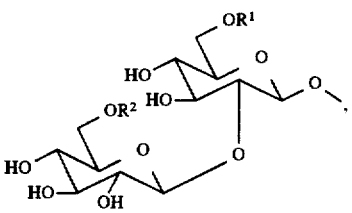

in the case where $R^4$ is a group of the formula II.

According to another aspect of the present invention, there has been provided, a process for the preparation of the compound described above which comprises:

fermenting a yeast with the ability to secrete sophorose-lipids in the form of a lactone into the culture supernatant being fermented in a culture medium which contains a 2-alkanol with a chain length of from 6 to 30 carbon atoms and an additional carbon source;

isolating the compound from the culture solution; and optionally subjecting the isolated compound to an alkaline hydrolysis.

DETAILED DESCRIPTION OF THE PREFERRED EMBODIMENTS

It has now been found, surprisingly, that novel, uncyclized glucose- and sophorose-lipids with surface-active properties are obtainable by fermentation of yeasts of the genus Candida by using 2-alkanols in place of the vegetable oils and fats, fatty acids or their alkyl esters. Thus, the present invention relates to a compound of formula I:

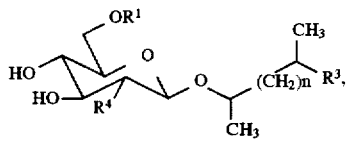

wherein the substituents are defined as above.

Preferred embodiments of the present invention are described hereinafter. Preferred embodiments include compounds of the formula I in which $R^4$ is a group of the formula II, where $R^1$ and $R^2$ jointly are —C(O)CH$_3$,
$R^1$ is H and $R^2$ is —C(O) CH$_3$,
$R^1$ is —C(O)CH$_3$ and $R^2$ is H or
$R^1$ and $R^2$ jointly are H, and
$R^3$ is H, —OH or a group of the formula III, and where n is an integer from 6 to 14, preferably 8 or 10.

Other preferred embodiments are compounds of the formula I in which $R^4$ is —OH, where $R^1$ is —C(O)CH$_3$ or H, $R^3$ is —OH or preferably H, and where n is an integer from 6 to 14, preferably 8 or 10.

The present invention furthermore relates to a process for the preparation of a compound of the formula I, where the variables $R^1$, $R^2$, $R^3$, $R^4$ and n have the stated meanings. In the process, a yeast with the ability to secrete sophorose-lipids in the form of a lactone into the culture supernatant, is fermented in a culture medium which, besides another carbon source such as glycerol, succinate or mono-, di- or trisaccharides, contains a 2-alkanol with a chain length of from 6 to 30 carbon atoms, after which the compound is isolated from the culture solution and, where appropriate, subjected to an alkaline hydrolysis.

The chain length of the 2-alkanol is generally from 6 to 30, preferably 10 to 18 carbon atoms, which makes it possible to prepare a compound of the formula I in which n is an integer from 6 to 14. 2-dodecanol or 2-tetradecanol is particularly preferably employed as alkanol, which makes it possible to prepare a compound of the formula I according to the above-mentioned numbers 1 or 2 (with n=8 or n=10).

It is possible to ferment in the process according to the present invention all yeast strains which secrete the sophorose-lipids which are described in the literature in lactone form (1) into the culture supernatant.

A yeast of the genus Candida is particularly suitable for the process according to the invention, and preferably *Candida bombicola*, *Candida bogoriensis*, *Candida magnoliae*, *Candida gropengiesseri* or *Candida apicola* is fermented.

Glucose or sucrose are particularly suitable as a carbon source.

The present invention furthermore relates to the use of a compound of the formula I in which $R^3$ is H or OH as surfactant.

According to another aspect of the present invention, there has been provided a surfactant which comprises the compound of the present invention.

Further objects, features and advantages of the present invention will become apparent from the detailed description of preferred embodiments which follows.

The use of 2-alkanols with chain lengths of generally from $C_6$ to $C_{30}$ as hydrophobic carbon source in addition to another carbon source such as, for example, glycerol, succinate or mono-, di- and trisaccharides such as, for example, sucrose, mannose, maltose, fructose, glucose and D-mannitol or other sugar alcohols. Glucose or sucrose is preferably used which results in the isolation of glucose- and sophorose-lipids with variation in the structure of the hydrophobic part of the molecule. The purified products in each case contain only lipid components with the chain length of the substrate employed in each case, with the latter either being directly incorporated into the glycolipid (compounds of structures 2 and 5 with $R^3$=H) or being linked, after an ($\omega$-1) hydroxylation as alkanediol via a glycosidic linkage to the sugar component (compounds of structure 3 or 5 with $R^3$=OH).

Production according to the invention results in exclusively nonionic surfactants with a typical surfactant structure.

The compounds of structure 3 can be converted by subsequent microbial reaction with a second sugar/sophorose unit into the compounds with structure 4. These very polar compounds have only slight surfactant properties.

The products are un-, mono- or diacetylated in the 6'—O and 6"—O position of the glucose unit in the sugar part. It is possible to obtain compounds corresponding to structures 2, 3, 4 and 5, in each case with n=2 to 26, by varying the chain length of the 2-alkanols employed (generally from $C_6$ to $C_{30}$). Structures 2–5 are illustrated below.

Accordingly, it is possible to prepare for example, on use of:

2-hexanol, a compound of the formula I with n=2,
2-octanol, a compound of the formula I with n=4,
2-decanol, a compound of the formula I with n=6,
2-undecanol, a compound of the formula I with n=7,
2-pentadecanol, a compound of the formula I with n=11,
2-octadecanol, a compound of the formula I with n=14,
2-eicosanol, a compound of the formula I with n=16
or on use of 2-triacontanol a compound of the formula I with n=26.

The 2-alkanols with chain lengths of C6 to C30 can, in some cases, be bought and can in some cases be prepared from the corresponding 2-alkanones or 1-alkenes which can be bought or the aldehydes of chain lengths $C_{n-1}$ (generally $C_n$=6 to 30) (*Organikum*, 16th edition, VEB-Deutscher Verlag der Wissenschaften 1986, which is incorporated by reference in its entirety, or other corresponding textbook of practical organic chemistry).

Thus, the corresponding 2-alkanones can be converted into the $C_6$–$C_{30}$-2-alkanols by catalytic hydrogenation with catalysis by Raney nickel in methanolic solution (*Organikum* 1986, page 432) or by reduction with lithium-aluminum hydride in ethereal solution (*Organikum* 1986, page 494).

The addition of water, catalyzed by a mercury salt, onto the double bond of 1-alkenes of chain lengths $C_6$ to $C_{30}$, the so-called oxymercuration reaction, likewise results in the corresponding secondary alkanols, the C6–C30-2-alkanols (*Organikum* 1986, page 257).

Furthermore, reduction of aldehydes of chain lengths $C_{n-1}$ (generally n=6 to 30) using methyllithium or using a methylmagnesium bromide Grignard reagent in ethereal solution provides the required 2-alkanol of chain length $C_n$ (generally n=6 to 30) (*Organikum* 1986, page 499).

Structures 2–5 described above are:

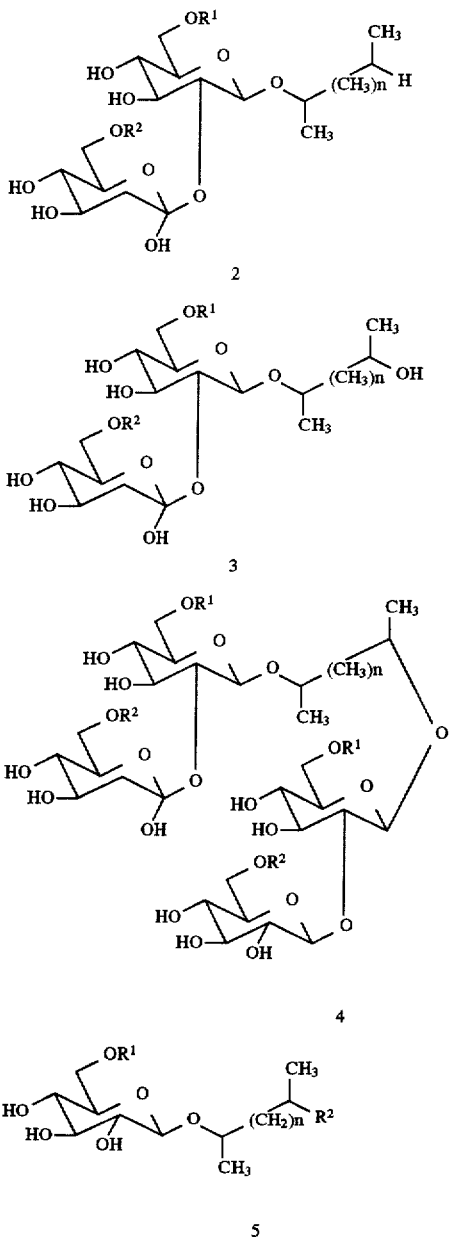

In structures:

2, 3, 4: n=2–26; $R^1$, $R^2$=H or —C(O)CH$_3$.

In structure: 5: n=2–26; $R^1$=H or —C(O)CH$_3$; $R^3$=H or —OH.

Specific preferred structures are as follows:

| | | |
|---|---|---|
| 2d: | $R^1 = R^2 = H$ | (see Examples 1 and 2: n = 10; Example 3: n = 8) |
| 2e: | $R^1 = $ —C(O)CH$_3$, $R^2 = H$ | (see Example 1: n = 10; Example 3: n = 8) |
| 2f: | $R^1 = R^2 = $ C(O)CH$_3$ | (see Example 1: n = 10; Example 3: n = 8) |
| 3g: | $R^1 = R^2 = H$ | (see Example 2: n = 10; Example 3: n = 8) |
| 3b: | $R^1 = $ —C(O)CH$_3$, $R^2 = H$ | (see Example 1: n = 10; Example 3: n = 8) |
| 3c: | $R^1 = R^2 = $ —C(O)CH$_3$ | (see Example 1: n = 10; Example 3: n = 8) |
| 4h: | $R^1 = R^2 = H$ | (see Example 2: n = 10; Example 3: n = 8) |
| 4a: | $R^1 = R^2 = $ —C(O)CH$_3$ | (see Example 1: n = 10; Example 3: n = 8) |
| 5a: | $R^1 = H$; $R^3 = H$ | (see Example 3: n = 8). |

At the end of the fermentation, the culture solution is preferably neutralized with an alkali, and the produced sophorose-lipids of structures 2–5 are preferably isolated by exhaustive extraction with a suitable solvent such as, for example, carboxylic esters such as ethyl acetate, butyl acetate or ethers such as tert-butyl methyl ether and diethyl ether or other solvents known to the skilled person.

The sophorose-lipids isolated in this way already have a distinctly higher solubility than classical products and bring about a greater reduction in the surface tension of water.

Alkaline hydrolysis with alkalis (for example aqueous NaOH) or alkanolates (for example sodium methanolate) can be used to convert the products acetylated in the 6'—O and 6"—O positions into the corresponding hydroxyl compounds.

The microorganisms which can be fermented are all yeast strains which secrete the sophorose-lipids described in the literature in the form of the lactone into the culture supernatant. Yeast strains which are preferably employed are *Candida bombicola, Candida bogoriensis, Candida magnoliae, Candida gropengiesseri* and *Candida apicola*.

The producer strains employed are fermented in a medium containing 2-alkanols with a chain length of generally $C_6$ to $C_{30}$, preferably $C_{10}$ to $C_{18}$. The concentration of 2-alkanols can be adjusted at the start of the fermentation or chosen to accord with the conversion rate by continuous replenishment. It has proven suitable to use sugars, preferably glucose or sucrose, to provide an additional carbon source. The medium should, besides the carbon source, also contain one or more nitrogen sources, sulfate and magnesium, and potassium, sodium, calcium and chloride ions, one or more phosphate sources, and a complex substrate promoting growth, such as, for example, yeast extract. The sugar is generally used in concentrations of 30 to 200 g/l of nutrient solution, with concentrations between 80 and 120 g/l being preferred. It is possible to use as a nitrogen source the nitrogen sources known to the skilled person, such as, for example, urea, ammonium chloride or ammonium sulfate in concentrations of 0.1 to 5 g/l of nutrient solution, with a concentration of 0.5–2.5 g/l preferably being chosen.

Generally, a 0.001 to 0.1 molar sodium phosphate or potassium phosphate buffer or a mixture of the two metal ions is employed as a phosphorus source and to buffer the medium. The pH of the culture solution decreases during the fermentation time.

If it is desired to isolate the products, the culture solution is, after removal of the biomass by centrifugation or filtration, preferably neutralized with an alkali and extracted, several times if required, with an organic solvent. The organic phases are removed, combined and dried over a desiccant such as, for example, sodium sulfate. Removal of the extractant in vacuo and azeotropic removal of the water result in a yellowish brown crude product.

The invention is explained in detail hereafter by means of the following exemplary embodiments.

EXAMPLE 1

To produce the biosurfactants, 400 ml of a culture medium of the following composition are introduced into a 2 l Erlenmeyer flask with baffles:

| | |
|---|---|
| Glucose.H$_2$O | 100 g/l |
| Sodium citrate.3 H$_2$O | 5 g/l |
| Yeast extract | 1 g/l |
| Ammonium chloride | 1.54 g/l |
| Potassium dihydrogen phosphate | 1 g/l |
| Magnesium sulfate.7 H$_2$O | 0.7 g/l |
| Sodium chloride | 0.5 g/l |
| Calcium chloride.2 H$_2$O | 0.27 g/l |
| Dipotassium hydrogen phosphate.3 H$_2$O | 0.16 g/l |

The medium is inoculated with the strain *Candida bombicola* ATCC 22214 and incubated on a rotary shaker at 100 rpm and a temperature of 30° C. After a cultivation time of 24, 48 and 72 h, in each case 10 g/l of 2-tetradecanol are added to the culture solution under aseptic conditions. The culture is carried out under unchanged conditions between and after the additions of the alcohol. The pH of the culture suspension decreases over the complete range of cultivation. After a cultivation period of 7 days, the supplied amount of alcohol is converted, and the cultivation is then terminated.

To isolate the products, the culture suspension is neutralized with 1 N sodium hydroxide solution and subsequently exhaustively extracted with ethyl acetate. The organic phases are separated off, combined and dried over anhydrous sodium sulfate. After removal of the desiccant on a paper filter, the solvent is removed by distillation under reduced pressure in a rotary evaporator. The remaining, highly viscous crude product is mixed with n-butanol for azeotropic removal of the bound water. It is subsequently completely removed by distillation again under reduced pressure. The solidified, virtually anhydrous, yellowish brown crude product is covered with twice the volume of dry diethyl ether and left to stand at room temperature for some hours. During this, the crude product decolorizes with a slight increase in volume to give an almost colorless solid which is covered by an orange-brown ether phase. After vigorous shaking, the solid is separated off on a paper filter, washed with a little ether and dried. The still somewhat tacky glycolipid mixture can be further standardized by washing with ice-water. It is obtained in a yield of 23 g/l.

The glycolipid mixture prepared in this way can be separated by thin-layer chromatography on silylated silica gel (RP-8) with the eluent mixture methanol/water 80:20 (v/v) into 6 single substances (compounds 4a, 3b, 3c, 2d, 2e and 2f, each with n=10) with characteristic R$_f$ values. It can be proven by nuclear magnetic resonance spectroscopy, FAB and TOF-SI mass spectrometry, and combined gas chromatography/mass spectrometry analysis of the hydrophobic part of the molecule (after acidic methanolysis) of the compounds that the individual compounds have the basic molecular structures 2, 3 and 4 (each with n=10) depicted. The main product of the cultivation is the compound with structure 2f (n=10).

Spectroscopic Data

| | |
|---|---|
| 4a: $^{13}$C-NMR (CD$_3$OD, 100 MHz, ppm): | 174.20 (s, —OCO—CH$_3$) |
| | 107.16/104.15 (2d, C-1'/C-1") |
| | 66.49/66.30 (2t, C-6'/C-6") |
| | 23.39 (q, C-1/14) |
| | 22.48/22.29 |
| | (q, —OCO—CH$_3$) |
| FAB-MS (Matrix NBA, pos., m/z): | 1069 (100, [M + Na]$^+$) |
| Lipid component: GC-MS (EI, m/z): | 212 (2, [M-H$_2$O]$^+$) |
| 2,13-Tetradecanediol | 45 (100, [CH$_3$CHOH]$^+$) |
| 3b: TOF-SIMS pos., m/z): | 619 (100, [M + Na]$^+$) |
| | 703 (34, [M + $^{107}$Ag]$^+$) |
| | 705 (27, [M + $^{109}$Ag]$^+$) |
| Lipid component: GC-MS (EI, m/z): | 212 (2, [M-H$_2$O]$^+$) |
| 2,13-Tetradecanediol | 45 (100, [CH$_3$CHOH]$^+$) |
| 3c: $^{13}$C-NMR (CD$_3$OD, 100 MHz, ppm): | 174.22 (s, —OCO—CH$_3$) |
| | 107.19/104.17 (2d, C-1'/C-1") |
| | 66.49/66.30 (2t, C-6'/C-6") |
| | 25.05 (q, C-14), |
| | 23.38 (q, C-1) |
| | 22.44/22.279 |
| | (q, —OCO—CH$_3$) |
| FAB-MS (Matrix NBA, pos., m/z): | 661 (100, [M + Na]$^+$) |
| Lipid component: GC-MS (EI, m/z): | 212 (2, M-H$_2$O]$^+$) |
| 2,13-Tetradecanediol | 45 (100, [CH$_3$CHOH]$^+$) |
| 2d: $^{13}$C-NMR (CD$_3$OD, 100 MHz, ppm): | 104.69/102.80 (2d, C-1'/C-1") |
| | 63.12/62.80 (2t, C-6'/C-6") |
| | 21.94 (q, C-1) |
| TOF-SIMS (pos., m/z): | 561 (100, [M + Na]$^+$) |
| | 645 (18, [M + $^{107}$Ag]$^+$) |
| | 647 (17, [M + $^{109}$Ag]$^+$) |
| Lipid component: GC-MS (EI), m/z): | 196 (1, [M-H$_2$O)$^+$) |
| 2-Tetradecanol | 45 (100, [CH$_3$CHOH]$^+$) |
| 2e: TOF-SIMS (pos., m/z): | 603 (100, [M + Na]$^+$) |
| | 687 (28, [M + $^{107}$Ag]$^+$) |
| | 689 (28, [M + $^{109}$Ag]$^+$) |
| Lipid component: GC-MS (EI, m/z): | 196 (1, [M + H$_2$O]$^+$) |
| 2-Tetradecanol | 45 (100, [CH$_3$CHOH]$^+$) |
| 2f: TOF-SIMS (pos., m/z): | 645 (100, M + Na]$^+$) |
| | 729 (32, [M + $^{107}$Ag]$^+$) |
| | 731 (30, [M + $^{109}$Ag]$^+$) |
| Lipid component: GC-MS (EI, m/z): | 196 (1, [M-H$_2$O]$^+$) |
| 2-Tetradecanol | 45 (190, [CH$_3$CHOH]$^+$) |

EXAMPLE 2

For basic hydrolysis of the sophorose-lipid isolated in Example 1, 10 g of the glycolipid mixture are dissolved in 300 ml of 1N sodium hydroxide solution and refluxed with stirring for 12 h.

Subsequently, the reaction mixture is neutralized with concentrated hydrochloric acid and cooled to 4° C. The precipitate which separates out is removed on a paper filter, washed with 100 ml of ice-cold water, and again taken up in 300 ml of water for recrystallization (60° C.→4° C). The recrystallized product is again filtered off and dried. The solid can be separated into two substances by chromatographic separation on silylated silica gel (RP-8) with the eluent system methanol/water 80:20 (v/v). Spectroscopic investigations on the fractionated substances prove that the less polar component has structure 2d (with n=10). The more polar component is the compound with structure 3g (with n=10).

The liquid part of the reaction mixture (1st filtrate) is extracted twice with twice the volume of ethyl acetate. The combined organic phases are dried over anhydrous sodium sulfate, and then the extractant is removed by distillation under reduced pressure. The yellowish brown, involatile residue is mixed with the same volume of n-butanol for azeotropic removal of the bound water. The residue after removal of the alcohol by distillation is a crude product which solidifies at room temperature. It contains another very polar sophorose-lipid which can be separated off by chromatography. It has structure 4h (with n=10) and corresponds in structure to a deacetylated 4a (n=10). In total, 6 g of deacetylated glycolipid are obtained, the major amount being the product of formula 2d (with n=10).

Spectroscopic Data

| | | |
|---|---|---|
| 2d: | See Example 1 | |
| 3g: | $^{13}$C-NMR (CD$_3$OD, 100 MHz, ppm): | 104.58/102.70 (2d, C-1'/C-1") |
| | | 63.01/62.69 (2t, C-6'/C-6") |
| | | 23.79 (q, C-14), |
| | | 21.84 (q, C-1) |
| | FAB-MS (neg., m/z): | 553 (100, [M-H]$^+$) |
| | Lipid component: GC-MS (EI, m/z): | 212 (2, M-H$_2$O]$^+$) |
| | 2,13-Tetradecanediol | 45 (100, [CH$_3$CHOH]$^+$) |
| 4h: | $^{13}$C-NMR (CD$_3$OD, 100 MHz, ppm): | 104.16/102.15 (2d, C-1'/C-1") |
| | | 63.18/62.12 (2t, C-6'/C-6") |
| | | 22.39 (q, C-1/14) |
| | FAB-MS (Matrix NBA, pos., m/z): | 901 (100, [M + Na]$^+$) |
| | Lipid component: GC-MS (EI, m/z): | 212 (2, M-H$_2$O]$^+$) |
| | 2,13-Tetradecanediol | 45 (100, [CH$_3$CHOH]$^+$) |

EXAMPLE 3

To produce the biosurfactants, 100 ml of a culture medium of the following composition are introduced into a 500 ml Erlenmeyer flask with baffles:

| | |
|---|---|
| Glucose.H$_2$O | 100 g/l |
| Sodium citrate.3 H$_2$O | 5 g/l |
| Yeast extract | 1 g/l |
| Ammonium chloride | 1.54 g/l |
| Potassium dihydrogen phosphate | 1 g/l |
| Magnesium sulfate.7 H$_2$O | 0.7 g/l |
| Sodium chloride | 0.5 g/l |
| Calcium chloride.2 H$_2$O | 0.27 g/l |
| Dipotassium hydrogen phosphate.3 H$_2$O | 0.16 g/l |

The medium is inoculated with the yeast *Candida bombicola* ATCC 22214 and incubated on a rotary shaker at 100 rpm and a temperature of 30° C. After a cultivation time of 24, 48 and 72 h, in each case 10 g/l of 2-dodecanol are added to the culture solution under aseptic conditions. The culture is carried out under unchanged conditions between and after the additions of the alcohol. The pH of the culture suspension decreases over the complete range of cultivation. After a cultivation period of 8 days, the supplied amount of alcohol is converted, and the cultivation is then terminated.

To isolate the products, the culture suspension is neutralized with 1 N sodium hydroxide solution and subsequently exhaustively extracted with ethyl acetate. The organic phases are separated off, combined and dried over anhydrous sodium sulfate. After removal of the desiccant on a paper filter, the solvent is removed by distillation under reduced pressure in a rotary evaporator. The remaining, highly viscous crude product is mixed with n-butanol for azeotropic removal of the bound water. It is subsequently completely removed by distillation again under reduced pressure. The solidified, virtually anhydrous, yellowish brown crude product is covered with twice the volume of dry diethyl ether and left to stand at room temperature for some hours. During this, the crude product decolorizes with a slight increase in volume to give an almost colorless solid which is covered by an orange-brown ether phase. After vigorous shaking, the solid is separated off on a paper filter, washed with a little ether and dried. The still somewhat tacky glycolipid mixture is further standardized by washing with ice-water. It is obtained in a yield of 18 g/l. It is able to reduce the surface tension of water at 25° C. from 72 to 29.5 mN/m (break point in the σ/c isotherms with 200 mg/l).

Where an aqueous solution of this glycolipid mixture which is saturated at 60° C. is allowed to cool to room temperature, fine, needle-like solid particles form in the solution. Crystallization is completed at 4° C. The needles are removed on a paper filter, and the filtrate is freeze dried to remove the solvent and recover the uncrystallized glycolipids.

The subsequent chromatographic separation of the non-crystalline portion on silylated silica gel (RP-8) with the eluent mixture methanol/water 80:20 (v/v) provides 6 single substances. Spectroscopic analysis of the individual substances proves that they have molecular structures 2, 3 and 4 (in each case with n=8) with a hydrophobic part of the molecule with a chain length of $C_{12}$. The main product of the cultivation in this case too is the compound of structure 2 f (with n=8).

After basic hydrolysis of the product mixture and chromatographic separation using the procedure as in Example 2, the products with structures 2 d, 3 g and 4 h (in each case with n=8) can be isolated.

As found by thin-layer chromatographic investigations on silylated silica gel (RP-8) with the eluent mixture methanol/water 80:20 (v/v), the crystallized part of the product mixture consists of another pure substance which has not hitherto been described. Nuclear magnetic resonance spectroscopy, FAB and TOF-SI mass spectrometry, and combined gas chromatographic/mass spectrometric analysis of the hydrophobic part of the molecule (after acidic methanolysis) of the compounds prove the presence of a glucose-lipid with molecular structure 5 a (n=8).

Spectroscopic Data

| | | |
|---|---|---|
| 5a: | $^{13}$C-NMR (CD$_3$OD, 100 MHz, ppm): | 102.36 (d, C-1') |
| | | 76.62 (d, C-3') |
| | | 76.30 (d, C-5') |
| | | 76.10 (d, C-2) |
| | | 73.79 (d, C-2') |
| | | 70.18 (q, C-4') |
| | | 61.30 (t, C-6') |
| | | 31.57–24.90 (8t, C-4-11) |
| | | 22.22 (t,C-3) |
| | | 20.44 (q, C-1) |
| | | 12.93 (q, C-12) |
| | FAB-MS (Matrix NBA, neg., m/z): | 153 (100, [NBA]$^-$) |
| | | 347 (32, [M-H]$^-$) |
| | | 501 (26, [M + NBA]$^-$) |
| | | 695 (6, [2M-H]$^-$) |
| | | 849 (1, [2M + NBA]$^-$) |
| | Lipid component: GC-MS (EI, m/z): | 168 (2, [M-H$_2$O]$^+$) |
| | 2-Dodecanol | 45 (100, [CH$_3$CHOH]$^+$) |

EXAMPLE 4

The surface activity of the surfactant properties of the glycolipid mixtures isolated as in Example 1 or Example 3 is documented by measuring their effect on the surface tension of water.

For this purpose, aqueous solutions of various concentrations c of the product mixtures are prepared, and their surface tension σ is measured using a ring tensiometer (from MGW Lauda, Lauda-Königshofen; de Noüy method without detachment) (σ/c isotherms).

Results

| c[mg/l] | σ [mN/m] Glycolipid mixture from Example 3 | σ [mN/m] Glycolipid mixture from Example 1 |
| --- | --- | --- |
| 500 | 29.5 | 30.8 |
| 300 | 29.6 | 30.8 |
| 200 | 29.8 | 30.9 |
| 100 | 31.1 | 31.6 |
| 50 | 33.0 | 32.8 |
| 10 | 45.2 | 39.3 |
| 5 | 50.8 | 46.2 |
| 1 | 60.4 | 57.0 |
| 0.5 | 65.0 | 60.5 |
| 0.1 | 68.5 | 66.2 |
| 0.01 | 70.3 | 70.0 |
| Dist. water | 72.0 | 72.0 |

Other embodiments of the invention will be apparent to those skilled in the art from consideration of the specification and practice of the invention disclosed herein. It is intended that the specification be considered as exemplary only, with the true scope and spirit of the invention being indicated by the following claims.

The texts of all publications mentioned above are expressly incorporated herein by reference in their entireties. Further, the text of German application No. 195 18 982.5 filed May 29, 1995 is hereby incorporated by reference in its entirety.

What is claimed is:

1. A compound of the formula I

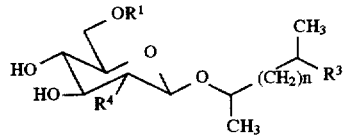   I in which $R^4$ is a group of the formula II,

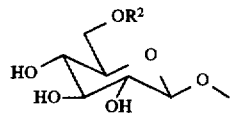

n is an integer from 2 to 26, $R^1$ and $R^2$ are, independently of one another, H or

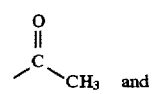  and $R^3$ is H or —OH or a group of the formula III.

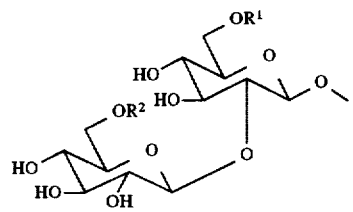   III

2. A compound as claimed in claim 1, wherein $R^1$ and $R^2$ are —C(O) $CH_3$.

3. A compound as claimed in claim 2, wherein $R^3$ is H.

4. A compound as claimed in claim 2, wherein $R^3$ is —OH.

5. A compound as claimed in claim 2, wherein $R^3$ is a group of the formula III.

6. A compound as claimed in claim 1, wherein $R^1$ is H and $R^2$ is —C(O) $CH_3$.

7. A compound as claimed in claim 1, wherein $R^1$ is —C(O)$CH_3$ and $R^2$ is H.

8. A compound as claimed in claim 1, wherein $R^1$ and $R^2$ are H.

9. A compound of the formula I

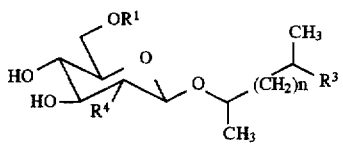   I in which $R^4$ is —OH n is an integer from 2 to 26, $R^1$ is

$R^2$ is H or

and $R^3$ is H or —OH.

10. A compound as claimed in claim 9, wherein $R^3$ is H.

11. A compound as claimed in claim 9, wherein $R^3$ is —OH.

12. A compound of the formula I

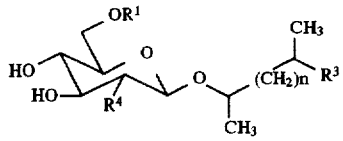   I in which $R^4$ is —OH or a group of the formula II,

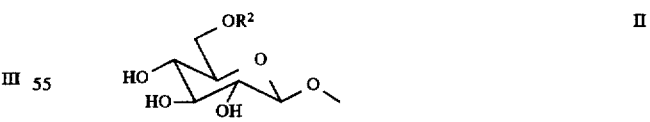   II n is an integer from 8 to 26, $R^1$ and $R^2$ are, independently of one another, H or

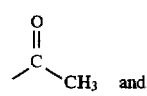  and $R^3$ is H or —OH in the case where $R^4$ is —OH, and is H or —OH or a group of the formula III

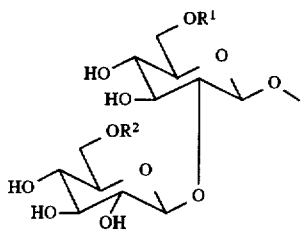

in the case where $R^4$ is a group of the formula II.

13. A compound as claimed in claim 12, wherein n is 8.
14. A compound as claimed in claim 12, wherein n is 10.
15. A process for the preparation of a compound of formula I

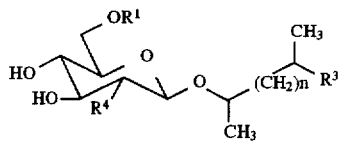

in which $R^4$ is —OH or a group of the formula II,

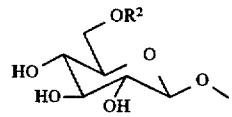

n is an integer from 2 to 26, $R^1$ and $R^2$ are, independently of one another, H or

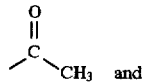

$R^3$ is H or —OH in the case where $R^4$ is —OH, and is H or —OH or a group of the formula III

in the case where $R^4$ is a group of the formula II, wherein the process comprises:

fermenting a yeast with the ability to secrete sophorose-lipids in the form of a lactone into the culture supernatant being fermented in a culture medium which contains a 2-alkanol with a chain length of from 6 to 30 carbon atoms and an additional carbon source;

isolating the compound from the culture solution; and optionally subjecting the isolated compound to an alkaline hydrolysis.

16. A process as claimed in claim 15, wherein n is an integer from 6 to 14, and wherein the chain length of the 2-alkanol is 10 to 18 carbon atoms.

17. A process as claimed in claim 16, wherein n is 8, and wherein 2-dodecanol is employed as the 2-alkanol.

18. A process as claimed in claim 16, wherein n is 10, and wherein 2-tetradecanol is employed as the 2-alkanol.

19. A process as claimed in claim 15, wherein a yeast of the genus Candida is fermented.

20. A process as claimed in claim 9, wherein the yeast is *Candida bombicola, Candida bogoriensis, Candida magnoliae, Candida gropengiesseri* or *Candida apicola*.

21. A process as claimed in claim 15, wherein the additional carbon source is one or more of glycerol, succinate, or mono-, di- or trisaccharides.

22. A process as claimed in claim 21, wherein glucose or sucrose is employed as the additional carbon source.

* * * * *